US00PP21935P3

(12) United States Plant Patent
Cavett

(10) Patent No.: US PP21,935 P3
(45) Date of Patent: May 31, 2011

(54) ***ACER FREEMANII×RUBRUM* NAMED 'JSC KINGSONE'**

(50) Latin Name: *Acer freemanii×rubrum*
Varietal Denomination: Shelina's Beauty

(76) Inventor: James David Cavett, Estill Springs, TN (US)

( * ) Notice: Subject to any disclaimer, the term of this patent is extended or adjusted under 35 U.S.C. 154(b) by 231 days.

(21) Appl. No.: 12/231,737

(22) Filed: Sep. 5, 2008

(65) Prior Publication Data

US 2010/0064401 P1 Mar. 11, 2010

(51) Int. Cl.
*A01H 5/00* (2006.01)

(52) U.S. Cl. ..... Plt./156

(58) Field of Classification Search ..... Plt./224
See application file for complete search history.

*Primary Examiner* — Wendy Haas

(74) *Attorney, Agent, or Firm* — Jason L. Hornkohl; Hornkohl Intellectual Property Law, PLLC

(57) ABSTRACT

A new and distinct *Acer freemanii×rubrum* cultivar, named the 'Shelina's Beauty' Maple is characterized by its variegated pigmentation of its leaves that varies with the age of the leaf, whereas trees of *Acer freemanii×rubrum* have no variegation known to the inventors. The 'Shelina's Beauty' Maple is also characterized by its drought and cold tolerance.

3 Drawing Sheets

Latin name: *Acer freemanii×rubrum.*
Varietal denomination: 'SHELINA's BEAUTY'.

FIELD OF THE INVENTION

The present invention comprises a new and distinct cultivar of *Acer freemanii×rubrum* and is referred to by the cultivar name 'Shelina's Beauty.'

BACKGROUND OF THE INVENTION

This new cultivar of *Acer freemanii×rubrum,* the 'Shelina's Beauty' maple, was originally discovered by James David Cavett on one specific tree limb of an *Acer freemanii×rubrum* tree planted in the yard of James Cavett at 74 S & W Lane, Estill Springs, Tenn. 37330, in 2004. James D. Cavett took a single cutting of the branch from the tree and rooted in sand using Hormondin #3 (active ingredient is indole-3-butyric acid) at 74 S&W Lane, Estill Springs, Tenn. 37330 in July 2004. In July 2005, 5 rooted cuttings were taken and rooted in sand at S&W Lane. Three of the 5 rooted cuttings survived. Sixty-seven rooted cuttings were started from the 3 surviving rooted cuttings in July 2006; these rooted cuttings were grown at 74 S&W Lane, Estill Springs, Tenn. 37330. Approximately 50 of the rooted cuttings begun in July 2006 survived and were used to begin 300 new rooted cuttings in the July 2007. In July 2008, approximately 1300 rooted cuttings were taken and rooted in sand; approximately 1000 rooted and survived. Over the last four years all the rooted cuttings of 'Shelina's Beauty' have exhibited the same growing characteristics and patterns as the parent plant *Acer freemanii×rubrum* except for the pigmentation of the leaves. The leaves of the rooted seedlings' pigmentation are red when the leaf breaks out of the bud. Within 3 weeks of budding, the leaves quickly turn a red-orange or crimson color. As the leaf enlarges, portions of it become yellow until the entire leaf becomes predominately cream in color. Older growth leaves have speckles of cream on a green background. James D. Cavett has been evaluating these propagated seedlings for 4 years.

James D. Cavett is solely responsible for finding this new cultivar on his property, located at 74 S&W Lane, Estill Springs, Tenn. 37330. All propagation of this cultivar has been done by James D. Cavett at his nursery located at 74 S&W Lane, Estill Springs, Tenn. 37330.

James D. Cavett immediately recognized that the new cultivar, 'Shelina's Beauty' exhibited new and distinctive leaf pigmentation. The leaves are red when they first erupt from the bud; however, within 3 weeks the leaf exhibits red-orange pigmentation. As the leaf enlarges and matures, the leaf pigmentation becomes yellow and the mature leaf is cream in color. All other growth characteristics of the cultivar are similar to the parent plant, *Acer freemanii×rubrum.* Only the seedlings that have originated from rooted cuttings of the original rooted stem that James D. Cavett rooted exhibit the leaf pigmentation that is attributed to the new cultivar, 'Shelina's Beauty.' Over the last 4 years, only the rooted cuttings have exhibited this pigmentation as compared to other *Acer freemanii×rubrum* trees.

FIG. 1 is a photograph of a year old 'Shelina's Beauty' seedling taken in July of 2007, which shows the distinctive and unique pigmentation of the leaves. The leaves that are coming out of the apical bud are red in color. The young leaves immediately below the apical leaves display a red-orange color. Leaves further down the stem, have a variegated yellow-green to green-yellow color. More mature leaves are also variegated and exhibit green and cream colors. Because the cultivar and the parent plant that it came from is deciduous, the leaves turn color (from rust-orange to a variegated burgundy mixture consisting of reds and pinks and light yellow) and drop off each fall in Zone 6b, which includes Middle Tennessee. As seen in more detail in FIGS. 2 and 3, the seedling has an alternate arrangement. The leaves are 8 cm to 15 cm in length and 5 cm to 18 cm in length. Thus, they are generally slightly wider than they are long. The leaves consist of 3 to 5 shallow lobes with shallow tooth margins. The petioles are red when the leaf first opens but turns green within several weeks. The diameter of petioles are ~0.3 to 0.4 cm and vary in length from 2 cm to 3.5 cm.

FIG. 2 is a photograph of a four year old 'Shelina's Beauty' tree taken in June of 2008 which also shows the distinctive and unique pigmentation of the leaves. As the tree matures, not all leaves will exhibit the same degree of variegation. Some leaves have more variegation than others. For example some will have more yellow than others. As also seen in FIG. 2, the 'Shelina's Beauty' cultivar is dense and full of foliage.

The 'Shelina's Beauty' cultivar has proven to be both drought resistant and very winter hardy. In April 2007, Middle Tennessee (climate Zone 6b, USDA Plant Hardiness Zone Map) experienced an unusually late freeze during which the overnight temperatures dropped into the low 20° F. This was a particularly dangerous and damaging freeze because most of the trees had already budded. The 'Shelina's Beauty' cultivar survived this freeze and continued to produce foliage throughout the spring and summer months. All rooted cuttings taken from the plants exhibit the same rapid growth that has been observed for the last 4 growing seasons that the 'Shelina's Beauty' cultivar has been cultivated.

The 'Shelina's Beauty' cultivar can also endure drastic changes in moisture. 'Shelina's Beauty' cultivar has been successfully grown without irrigation after it is moved into the fields during its second season. Each summer since it was rooted in 2004, it has endured the drought that Middle Tennessee has experienced during the months of July and August. Middle Tennessee usually experiences heavy rainfalls during the spring; however, immediately after the late spring 2007 freeze another unusual meteorological event occurred; Middle Tennessee experienced a 2 month drought. While many annuals, perennials, shrubs, and trees were severely damaged or killed by the late spring freeze that was followed by a 2-month drought, the 'Shelina's Beauty' cultivar survived and demonstrated itself to be cold and drought tolerant.

The 'Shelina's Beauty' cultivar has been successfully propagated asexually. The proven means of asexual propagation has been rooted softwood cuttings. During the first year the stem that was discovered by James D. Cavett was rooted in sand at his nursery located at 74 S&W Lane, Estill Springs, Tenn. 37330. Because only one stem on the parent plant exhibited the identifying pigmented foliage, only one cutting was stuck in 2004. In July 2005, 5 rooted cuttings were taken from the one year old original stem and stuck in sand by James D. Cavett at his nursery and 3 survived. In July 2006, 67 rooted cuttings were started from the other 'Shelina's Beauty' trees that had been rooted in 2004 and 2005, and 50 survived. In July 2007, 300 out of 400 cuttings taken from the other 'Shelina's Beauty' trees were rooted and survived. In July 2008, 1300 rooted cuttings were taken from the other 'Shelina's Beauty' trees and stuck in sand, and approximately 1000 survived. The cultivars have retained all the characteristics of the original selected seedling. It has been successfully propagated through 5 generations of asexual reproduction with a survival rate between 60% the second year (2005), 75% the third year (2006), 75% the fourth year (2007), and a 77% survival rate in 2008. Each generation has been stable and produced true-to-type plants each and every time the plant has been propagated.

The unique color of the leaves and rapid growth (3 to 5 feet per year) 'Shelina's Beauty' cultivar make it well suited for a variety of landscaping uses. Furthermore, the 'Shelina's Beauty' cultivar is cold and drought tolerant. The cultivar is a moderate size tree whose leaf pigmentation transitions from red when the bud opens to orange-red in approximately 3 weeks, followed by a variegated yellow-green and final a variegated cream and green color in the mature leaf. In the fall the leaves turn from a variegated cream on a green background to a burgundy mixture consisting of reds and pinks with a light yellow in the creamy variegated portion of the leaf. The unique color of the leaves of the 'Shelina's Beauty' cultivar will make it a popular maple tree for those who desire attractive coloration from early spring through the fall.

SUMMARY OF THE INVENTION

The following characteristics in combination distinguish the new tree named 'Shelina's Beauty' cultivar from other cultivars of *Acer freemanii×rubrum.*

1. The 'Shelina's Beauty' cultivar has as a distinctive and unique variegated leaf that the parent plant, *Acer freemanii×rubrum,* and other cultivars of *Acer freemanii× rubrum* known to the inventors do not have. The colors of the leaves change throughout the growing season, culminating with a variegated cream-green pattern in the mature leaf in late summer/early fall.
2. With the distinctive, variegated foliage color that changes throughout the growing season, the 'Shelina's Beauty' cultivar will be a popular tree for landscaping applications.
3. The 'Shelina's Beauty' cultivar is cold tolerant. It has withstood very low 20 degree F. temperatures in late April, long after the leaf buds opened. Most trees in Middle Tennessee were severely damaged during this cold spell that occurred so late in the spring (2007).
4. The 'Shelina's Beauty' cultivar is able to endure drastic changes in moisture levels. There is usually heavy rainfall in the spring and very little rain in July and August in Middle Tennessee (climate Zone 6b, USDA Plant Hardiness Zone Map). However, in 2007 there was little rain in the spring and late summer, and the cultivar thrived. Furthermore, throughout the summer 2007 many days broke the record high temperature for the day.
5. The 'Shelina's Beauty' cultivar grows rapidly. The seedlings grew 3 to 5 feet during their first year and 8 to 9 feet during their second year. During their third year, their average truck size measured 4.38 cm.
6. After 4 years of growth, the 'Shelina's Beauty' cultivar has remained insect and pathogen resistant growing in the fields of Middle Tennessee.
7. The 'Shelina's Beauty' cultivar has not been observed under all conditions, and it is not known how the cultivar might respond to various conditions.

DETAILED BOTANICAL DESCRIPTION

Figure 1:
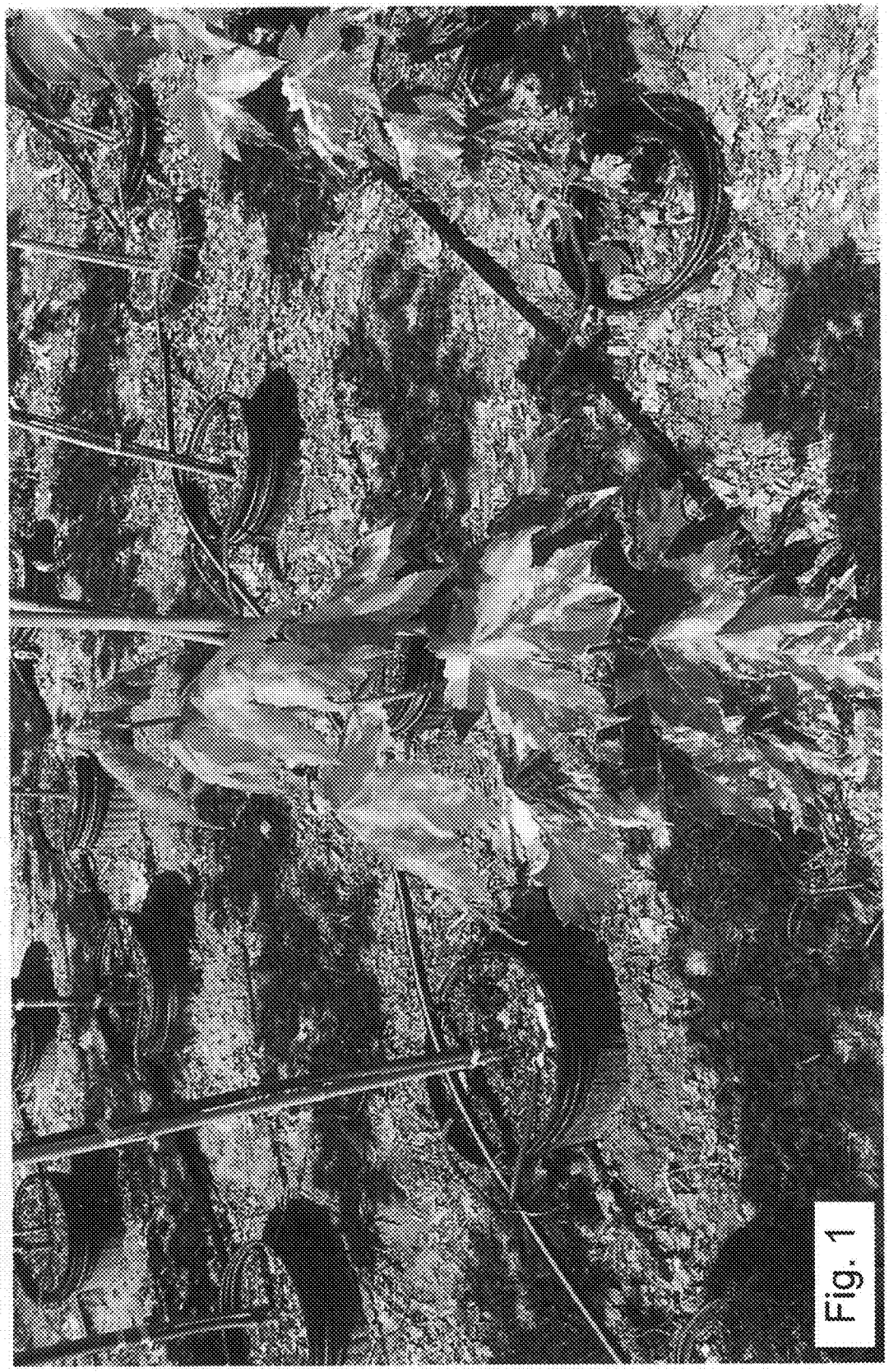
FIG. 1 shows the red leaves as they emerge from the apical leaf bud and the yellow-green and cream-green variegated leaves as one move from the top of the seedling to the base of the tree. This seedling is one of fifty that James D. Cavett rooted in July 2006 at 74 S&W Lane, Estill Springs, Tenn. 37330.
Figure 2:
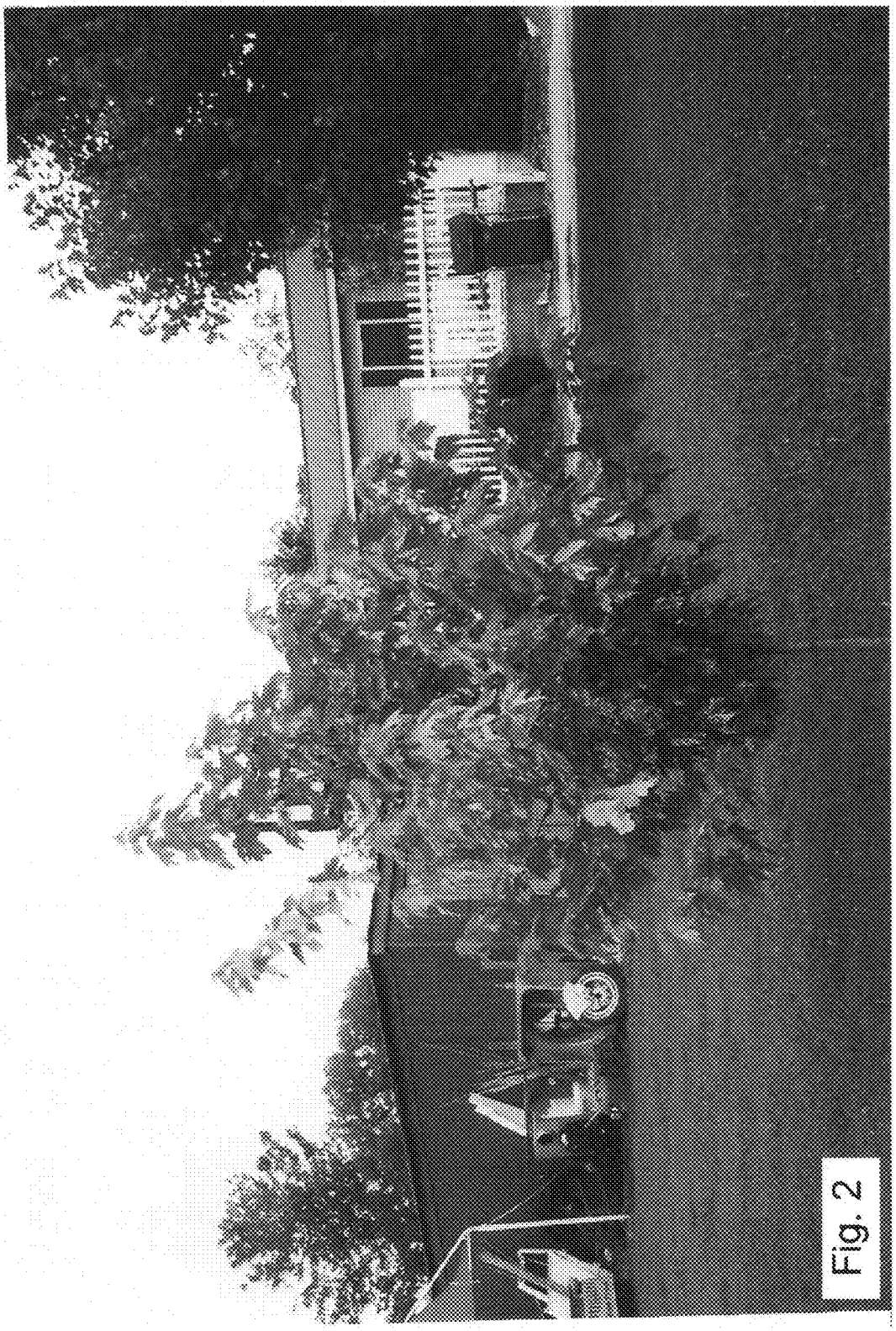
FIG. 2 shows the originally discovered 'Shelina's Beauty' as it looks in 2008, four years after its discovery at 74 S&W Lane, Estill Springs, Tenn. 37330.
Figure 3:
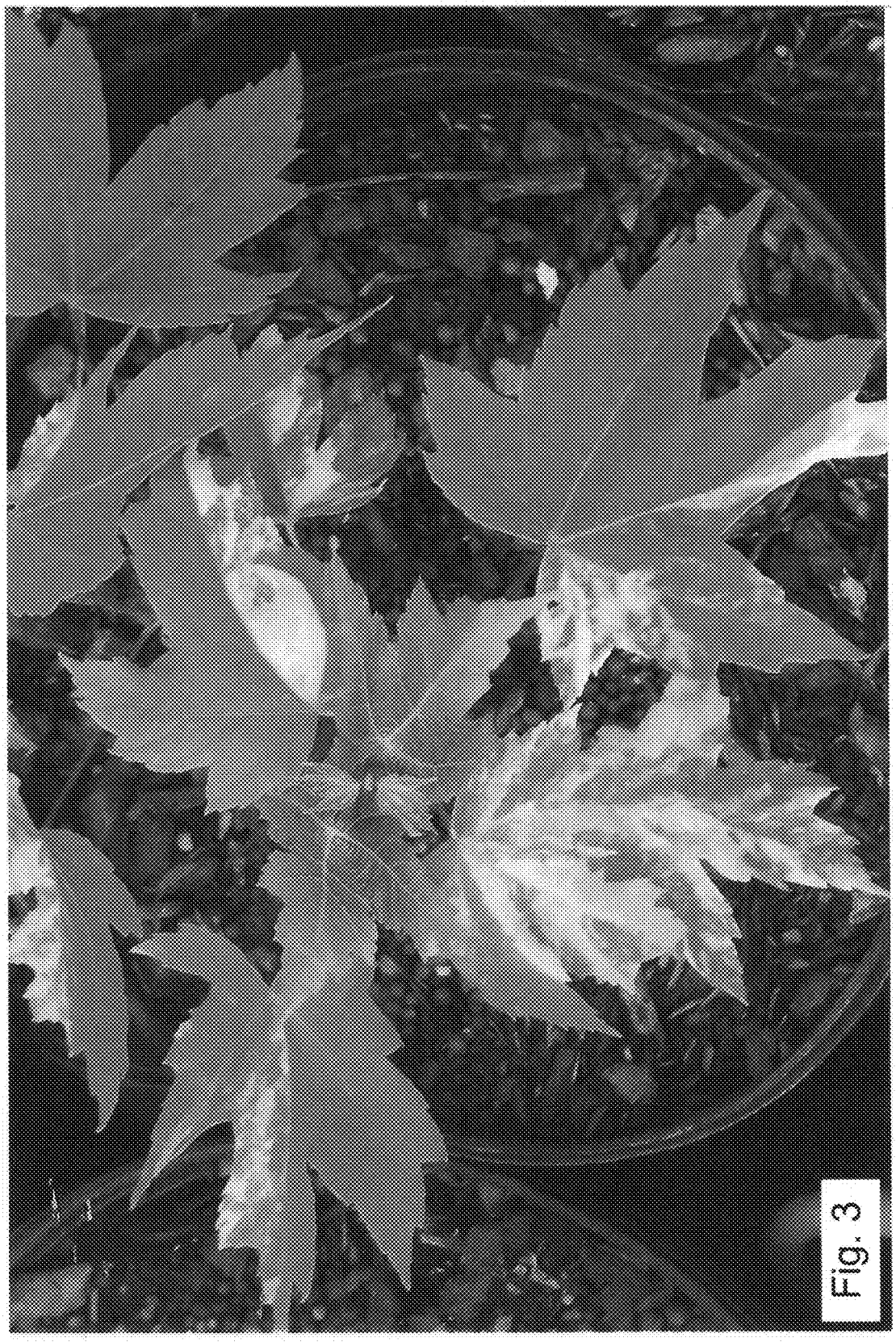
FIG. 3 is a closer view of the leaf color a couple of weeks after the leaf emerges from its bud. Several of the younger leaves exhibit the characteristic orange-red and green colors.

The following observations, measurements, and values describe plants grown at 74 S&W Lane, Estill Springs, Tenn.

37330. The actual appearance and characteristics of any individual plant will vary due to horticultural practices and local conditions. The tree used to description is four years old. Color references are made to The Royal Horticultural Society Colour Chart except where terms of ordinary significance are used.

Botanical classification: *Acer freemanii×rubrum.*

Commercial classification: 'Shelina's Beauty' maple.

Origin: One specific branch that had variegated leaf colors was cut from the parental plant, an *Acer freemanii×rubrum.* (This specific branch was the sole branch on the tree that exhibited variegation.

Parentage: Cutting of a stem from *Acer freemanii×rubrum.*

Propagation: Asexual by softwood cuttings.

Plant:

*Growth rate.*—Fast; an average of 3 to 5 feet per year or 100 to 160 cm.

*Form.*—Oval.

*Shape.*—Oval to round.

*Height.*—Average size of the *Acer freemanii×rubrum* is 1200 to 1800 cm.

*Spread.*—Average size of the *Acer freemanii×rubrum* is 900 to 1200 cm.

*Density.*—Thick with foliage.

*Trunk size.*—4.4 cm diameter at the base of the trunk at ground level after 4 years. The color of the bark on the truck of a four-year old tree varies from N200C — RHS to N202C — RHS.

*Bark.*—(Trunk): smooth, color is (N199C — RHS) textured with tiny raised lenticels.

*Branching arrangement.*—Opposite. Angel of attachment: Ranges from 45 to 60 degrees with 45 degrees being most prevalent. Internodal length: Mature branches range from 3.5 to 5.0 inches or 8.5 to 9.0 cm on a year-old seedling. The average length of a typical branch is 44 inches or 110 cm on a 5-year old tree.

*Stem.*—On the mature stems, the color is (171A — RHS) on the 1-year old seedling. Typical observed length is up to 9.0 cm, diameter is from 0.4 to 0.5 cm. On the new growth, the stem color is a mixture of two colors (the youngest portion of the stem is 44A — RHS) and (the older portion of the stem is 171A — RHS). The arrangement of leaves is opposite. The length of new growth stem on a five-year old seeding is averages 37 cm with a diameter of 0.4 to 0.5 cm. The internodal length on the 5-year old plant varies from 8.0 cm to 11.3 cm. and average 9.5 cm.

*Lenticels.*—Small, but conspicuous, light brown to silver in color. They are 1 to 2 mm in length and 0.5 to 1.0 in width. The color of the lenticels is 202C — RHS.

*Leaves.*—Deciduous.

*Leaf length.*—Petioles vary from 5 cm to 6.0 cm on young leaves, but average 5.5 cm; Leaf length varies from 7.6 cm to 17.8 cm in length and 7.6 cm to 16.5 cm in width. The color of the petiole is (45A — RHS) when the leaf first opens but the mature petiole is (47A — RHS) in color and has an average diameter of 0.3 cm.

*Average leaf width.*—9 cm on growing branch tips (near the aprical meristem) and 17 cm at the base of the branch.

*Leaf shape.*—Lobed with 3 or 5 shallow lobes.

*Leaf margin.*—Tooth.

*Leaf texture.*—Smooth on the upper and lower surfaces of the leaf, the lower surface has some hairs.

*Leaf quantity.*—Abundant.

*Leaf color.*—The most apical, leaves that have emerged from the apical meristem is red (41A — RHS) that is muted by the chlorophyll that is forming. Upper side of new growth (3-week old leaves): the 3-week old leaves it is a mixture of (179A — RHS) and (163A — RHS); the upper side of the most mature leaves have a mixture of (137A — RHS) and (157A — RHS) or (145A — RHS). Lower side of the leaf: the color mixture is similar to the upper side at early leaf ages but changes in the most mature leaves to a mixture of (194A — RHS) and (4D — RHS) or (8C — RHS).

*Leaf ribs and veins.*—Upper rib surface at the petiole end of the leaf is red (53C — RHS) to greenish-white (146C — RHS) at the tip of the leaf. The lower rib surface (leaf underside) color is (53C — RHS) at the petiole end of leaf and (145B — RHS) at the tip of the leaf. Venation is netted.

*Vegetative buds.*—Terminal bud or apical bud is 145B — RHS. Lateral buds are conical and 3 to 4 mm in length and brown to greenish brown in color (15B — RHS).

*Leaf apex.*—The leaf apex is acute, and the apical bud is 145B — RHS.

*Base descriptor.*—Rounded.

Flowers: Seedless.

Disease and pest resistance: No known susceptibility to diseases or pests common to *Acer freemanii×rubrum.*

I claim:

1. A new and distinct cultivar of *Acer freemanii×rubrum* tree named 'Shelina's Beauty' as illustrated and described herein.

* * * * *